(12) United States Patent
Fujimoto et al.

(10) Patent No.: US 10,059,654 B2
(45) Date of Patent: Aug. 28, 2018

(54) COMPOSITION CONTAINING 3-CHLORO-4-METHOXYBENZYLAMINE HYDROCHLORIDE, AND METHOD FOR PRODUCING SAME

(71) Applicant: AIR WATER INC., Sapporo-shi, Hokkaido (JP)

(72) Inventors: Takashi Fujimoto, Kashima (JP); Keiichi Yokota, Kashima (JP); Takahiro Ide, Kashima (JP)

(73) Assignee: AIR WATER INC., Sapporo-shi (JP)

( * ) Notice: Subject to any disclaimer, the term of this patent is extended or adjusted under 35 U.S.C. 154(b) by 0 days.

(21) Appl. No.: 15/730,317

(22) Filed: Oct. 11, 2017

(65) Prior Publication Data
US 2018/0029974 A1    Feb. 1, 2018

Related U.S. Application Data

(62) Division of application No. 15/306,646, filed as application No. PCT/JP2014/061994 on Apr. 30, 2014.

(51) Int. Cl.
C07C 213/08    (2006.01)
C07C 217/58    (2006.01)
C07C 213/10    (2006.01)

(52) U.S. Cl.
CPC .......... C07C 213/08 (2013.01); C07C 213/10 (2013.01); C07C 217/58 (2013.01)

(58) Field of Classification Search
None
See application file for complete search history.

(56) References Cited

U.S. PATENT DOCUMENTS 4,683,346 A    7/1987  Ratton
6,316,438 B1   11/2001 Yu et al.

FOREIGN PATENT DOCUMENTS

| JP | 61-145136 A | 7/1986 |
|----|-------------|--------|
| JP | 62-223140 A | 10/1987 |
| JP | 2002-540102 A | 11/2002 |
| SU | 386891 A | 6/1973 |
| SU | 451685 A | 11/1974 |

OTHER PUBLICATIONS

Watanabe et al., "4-Benzylamino-1-chloro-6-substituted Phthalazines: Synthesis and Inhibitory Activity toward Phosphodiesterase 5", J. Met Chem. (1998), vol. 41, pp. 3367-3372.
Endo et al., "Practical Preparation of 3-chloro-4-Methoxybenzylamine Hydrochloride", Synthetic Communications: An International Journal for Rapid Communication of Synthetic Organic Chemistry, 2000, 30 (14), pp. 2609-2612.
Vyas et al., "Environmentally benign chlorination and bromination of aromatic amines, hydrocarbons and naphthols", Tetrahedron Letters, 2003, 44 (21), pp. 4085-4088.
Koini et al., "Simple and Efficient Method for the Halogenation of Oxygenated Aromatic Compounds", SYNLETT, 2011, (11), pp. 1537-1542.
International Search Report and Written Opinion, International Patent Application No. PCT/JP2014/061994 with English translation (14 pages).
English translation of first Office Action issued for corresponding Japanese application No. 2016-515801, dated Dec. 26, 2017 (3 pages).
Extended European Search Report, European Patent Application No. 14891029.2, dated May 4, 2018 (10 pages).
Smith et al., "Design, synthesis, and evaluation of azepine-based cryptophycin mimetics", Tetrahedron, vol. 59, pp. 6991-7009, Jul. 29, 2003.
Yu et al., "Substitute Pyrazolopyridines as Potent and Selective PDE5 Inhibitors: Potential Agents for Treatment of Erectile Dysfunction", J. Med. Chem. vol. 44, pp. 1025-1027, Jun. 3, 2001.
Watanabe et al., "4-Benzylamino-1-chloro-6-substituted Phthalazines: Synthesis and Inhibitory Activity Towards Phosphodiesterase 5" J. Med. Chem., vol. 41, pp. 3367-3372, May 8, 1998.

*Primary Examiner* — Clinton A Brooks
(74) *Attorney, Agent, or Firm* — Hamre, Schumann, Mueller & Larson, P.C.

(57) ABSTRACT

There is provided a method for producing, at a high yield, a composition containing 3-chloro-4-methoxybenzylamine hydrochloride (CMBA-HCl) in which the purity of CMBA-HCl is high. This method comprises a chlorination step involving a chlorination reaction that generates CMBA-HCl from 4-methoxybenzylamine hydrochloride using hydrogen peroxide and hydrochloric acid. There is also provided a CMBA-HCl-containing composition which is produced by the aforementioned production method and in which the purity of CMBA-HCl is high.

5 Claims, No Drawings

COMPOSITION CONTAINING 3-CHLORO-4-METHOXYBENZYLAMINE HYDROCHLORIDE, AND METHOD FOR PRODUCING SAME

TECHNICAL FIELD

The present invention relates to a composition containing 3-chloro-4-methoxybenzylamine hydrochloride which can be used as an intermediate for medicines or the like and a method for producing the same.

BACKGROUND ART

Hydrochloride of 3-chloro-4-methoxybenzylamine (3-chloro-4-methoxybenzylamine will also be referred to as "CMBA" in the present description) (hydrochloride of 3-chloro-4-methoxybenzylamine hydrochloride will also be referred to as "CMBA-HCl" in the present description) is an important compound that can be used as an intermediate for various medicines. Non-Patent Literature 1 discloses a method for producing a composition containing 3-chloro-4-methoxybenzylamine hydrochloride (also referred to as a "CMBA-HCl-containing composition" in the present description) which is a composition that contains the CMBA-HCl. This method includes chlorinating 4-methoxybenzaldehyde (also referred to as "MB" in the present description) as a reactant using sulfuryl chloride to obtain 3-chloro-4-methoxybenzaldehyde (also referred to as "CMB" in the present description), converting aldehyde groups of the CMB to formamide groups using formamide and formic acid to obtain N-(3-chloro-4-methoxybenzyl)formamide (also referred to as "CMBF" in the present description), and further reacting the CMBF and hydrochloric acid under the presence of ethanol and the like to obtain a composition containing 3-chloro-4-methoxybenzylamine hydrochloride, that is, the CMBA-HCl-containing composition.

Patent Literature 1 discloses a method for obtaining a CMBA-HCl-containing composition using 4-methoxybenzylamine (also referred to as "MBA" in the present description) as a starting material through a method of blowing chlorine gas into the starting material or a method of reacting the starting material with sulfuryl chloride.

PRIOR ART LITERATURE

Patent Literature

[Patent Literature 1] U.S. Pat. No. 6,316,438B

Non-Patent Literature

[Non-Patent Literature 1] J. Med. Chem. (1998), vol. 41, pp 3367-3372

SUMMARY OF THE INVENTION

Problems to be Solved by the Invention

However, the production method for a CMBA-HCl-containing composition as described in Non-Patent Literature 1 involves a number of steps and thus has a problem of low yield. That is, the yield in the production method for obtaining a crude composition containing the CMBA-HCl via the MB as the reactant, CMB and CMBF is up to about 44% even with reference to the production results at a laboratory level as described in Non-Patent Literature 1. When the present inventors confirmed this production method at an industrial production scale, the yield of the above crude composition was only about 33%. It also became apparent that the purity of the CMBA-HCl in the above crude composition, which was obtained from the content calculated on the basis of the peak area ratio obtained by the GC measurement, is about 90% and the method cannot be said to be a manufacturing technique at industrial levels. The reason that the yield is thus low may be because impurities remain, such as substances based on inappropriate chlorination of the MB and by-products which are presumed to be dimerization products of the CMBF.

In view of such actual circumstances, an objective of the present invention is to provide a method for producing, at a high yield, a CMBA-HCl-containing composition in which the content of CMBA-HCl represented by Chemical Formula 1 below is high. Another objective of the present invention is to provide a CMBA-HCl-containing composition which is produced by the method for producing and in which the purity of CMBA-HCl is high.

[Chemical Formula 1]

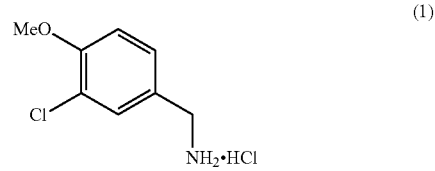

(1)

Means For Solving the Problems

As a result of intensive studies for solving the above problems, the present inventors have acquired the following knowledge.

(1) A CMBA-HCl-containing composition in which the impurity concentration is low can be produced at a high yield and in a simplified manner by changing the reactant from the MB to 4-methoxybenzylamine hydrochloride (also referred to as "MBA-HCl" in the present description) that allows a highly-pure product to be readily obtained and chlorinating the MBA-HCl using hydrogen peroxide and hydrochloric acid.

(2) A CMBA-HCl-containing composition in which the impurity concentration is particularly reduced can be obtained by recrystallizing the CMBA-HCl-containing composition, which is produced by the above method, under the presence of a tertiary amine.

The present invention accomplished by such knowledge is as follows:

(1) A method for producing a composition containing 3-chloro-4-methoxybenzylamine hydrochloride, the method being characterized by comprising a chlorination step involving a chlorination reaction that generates 3-chloro-4-methoxybenzylamine hydrochloride from 4-methoxybenzylamine hydrochloride using hydrogen peroxide and hydrochloric acid.

(2) A method for producing a composition containing 3-chloro-4-methoxybenzylamine hydrochloride, the method comprising a purification step of recrystallizing a composition containing 3-chloro-4-methoxybenzylamine hydrochloride using a solvent containing a tertiary amine.

(3) A method for producing a composition containing 3-chloro-4-methoxybenzylamine hydrochloride, the method being characterized by comprising: a chlorination step involving a chlorination reaction that generates 3-chloro-4-methoxybenzylamine hydrochloride from 4-methoxybenzylamine hydrochloride using hydrogen peroxide and hydrochloric acid; and a purification step of recrystallizing a generated product obtained by the chlorination step, using a solvent containing a tertiary amine.

(4) The method for producing as described in the above (1) or (3), wherein a starting material for the chlorination reaction is a composition containing 4-methoxybenzylamine hydrochloride and a content of the 4-methoxybenzylamine hydrochloride is 99.5% or more as a content based on a peak area ratio obtained by HPLC measurement.

(5) The method for producing as described in the above (2) or (3), wherein the purification step includes reducing a content of one or more selected from the group consisting of 3,5-dichloro-4-methoxybenzylamine and its derivatives.

(6) A composition containing 3-chloro-4-methoxybenzylamine hydrochloride produced by the method for producing as described in any one of the above (1) to (5).

Advantageous Effect of the Invention

According to the present invention, there is provided a method for producing, at a high yield, a CMBA-HCl-containing composition in which the purity of CMBA-HCl is high. There is also provided a CMBA-HCl-containing composition which is produced by the method for producing and in which the purity of CMBA-HCl is high.

EMBODIMENTS FOR CARRYING OUT THE INVENTION

Hereinafter, an embodiment of the present invention will be described in detail.

1. Method for Producing CMBA-HCl-Containing Composition

The method for producing a CMBA-HCl-containing composition according to the present embodiment includes a chlorination step and a recrystallization step, which are to be described below. In a chlorination reaction that is carried out in the chlorination step, MBA-HCl is the reactant. Therefore, the MBA-HCl will first be described and the above two steps and other steps will then be described.

(1) MBA-HCl

As the above, in the chlorination reaction carried out in the chlorination step included in the method for producing a CMBA-HCl-containing composition according to the present embodiment, MBA-HCl (4-methoxybenzylamine hydrochloride) is the reactant. An MBA-HCl-containing composition, which is a composition that contains MBA-HCl (and which may also be referred to as a "4-methoxybenzylamine hydrochloride-containing composition" in the present description), is sold in a market and available readily and stably from the market and may be used as the starting material for the chlorination reaction step carried out in the chlorination step. The purity of MBA-HCl in the MBA-HCl-containing composition used as the starting material for the chlorination reaction is not particularly limited, but an MBA-HCl-containing composition of purity of 99.5% or more can readily be available at low cost because it is possible to increase the purity in the step of obtaining MBA-HCl from MBA. In the present description, the "purity" of MBA-HCl and CMBA-HCl refers to the purity obtained from the content based on a peak area ratio that is obtained by performing HPLC measurement using a measurement method as stated in the examples to be described later.

In this context, the starting material in the method described in Non-Patent Literature 1 is a material that contains MB, but this starting material may contain impurities such as dimerization products of MB. Such impurities and/or components based on such impurities are difficult to remove in the subsequent steps (such as the step involving a reaction that generates CMB from MB, the step involving a reaction that generates CMBF from CMB, and the step involving a reaction that generates CMBA-HCl from CMBF), which may cause a high concentration of impurities in the obtained CMBA-HCl-containing composition.

In contrast, according to the production method of the present embodiment using an MBA-HCl-containing composition, impurities such as dimerization products of MBA and substances based thereon are stably removed in the step involving a reaction that obtains MBA-HCl from MBA. Thus, the MBA-HCl-containing composition can be used as the starting material thereby to reduce the concentration of impurities in the CMBA-HCl-containing composition which is the objective substance.

(2) Chlorination Step

The method for producing a CMBA-HCl-containing composition according to the present embodiment includes a chlorination step involving a chlorination reaction that uses an MBA-HCl-containing composition as the starting material and generates CMBA-HCl from MBA-HCL contained in the starting material using hydrogen peroxide and hydrochloric acid. That is, in contrast to Non-Patent Literature 1 in which three steps each involving a chemical reaction are necessary to obtain a CMBA-HCl-containing composition from the starting material, the method for producing a CMBA-HCl-containing composition according to the present embodiment needs only one step involving a chemical reaction from the starting material, thereby to allow the CMBA-HCl-containing composition to be obtained. As will be understood, increase in the number of steps each involving a chemical reaction may make the production method complex and reduce the productivity, yield and purity. Therefore, the method for producing a CMBA-HCl-containing composition according to the present embodiment can be said to be an excellent method compared with the method for producing a CMBA-HCl-containing composition according to the prior art at least from the point that the number of steps each involving a chemical reaction is reduced.

The chlorination reaction is carried out as below.

First, the MBA-HCl-containing composition is dissolved in a polar solvent such as water to obtain an MBA-containing solution. Typical example of the solvent is water as the above and another polar solvent such as alcohol may be contained therein as necessary. Mass ratio of the solvent to the MBA-HCl (solvent/MBA-HCl) in the MBA-containing solution is not particularly limited. If the mass ratio is unduly low, homogeneous chlorination reaction will be difficult, while if the mass ratio is unduly high, the occurrence of disadvantages will possibly be high, such as an increased amount of the waste liquid and a prolonged time for the reaction. Therefore, in consideration of such a tendency, the above mass ratio may be appropriately set. In general, this mass ratio may appropriately be set within a range of about 1.5 times to about 10 times, preferably within a range of twice to 8 times, and more preferably within a range of 2.5 times to 6 times.

Next, a solution that contains hydrochloric acid (also referred to as a "hydrochloric acid solution" in the present description) is dropped into the MBA-containing solution which is stirred at a temperature within a range of 5° C. to 70° C. and preferably 10° C. to 60° C. Solvent of the hydrochloric acid solution is ordinarily water, but is not limited to water, as in the MBA-containing solution. The amount of dropping the hydrochloric acid solution may be such that the ratio of the number of moles of the dropped hydrochloric acid to the number of moles of MBA-HCl contained in the MBA-HCl-containing solution (hydrochloric acid/MBA-HCl) is preferably about 1.5 or more and about 4 or less and more preferably 2 or more and 3 or less. The concentration of hydrochloric acid in the hydrochloric acid solution is not particularly limited. If the concentration of hydrochloric acid is unduly low, the possibility of a prolonged time for the reaction and/or a reduced reactivity will be high because the amount of dropping the hydrochloric acid solution increases, while if the concentration of hydrochloric acid is unduly high, the homogeneity of reaction will possibly be low. Therefore, in consideration of such a tendency, the above concentration of hydrochloric acid may be appropriately set. In general, the concentration of hydrochloric acid in the above hydrochloric acid solution may preferably be 10 mass % or more and 60 mass % or less and more preferably 20 mass % or more and 50 mass % or less. The dropping time for the hydrochloric acid solution may appropriately be set with consideration for the concentration of hydrochloric acid in the hydrochloric acid solution, etc. An example of the dropping time may be about 0.5 to 1 hour.

Subsequently, a solution that contains hydrogen peroxide (also referred to as a "hydrogen peroxide solution" in the present description) is dropped into the MBA-containing solution which is stirred and into which the hydrochloric acid solution has been dropped, while the temperature of the MBA-containing solution is maintained within a range of 60° C. to 70° C. and preferably 62° C. to 68° C. Solvent of the hydrogen peroxide solution is ordinarily water, but is not limited to water, as in the MBA-containing solution. Since the temperature of the MBA-containing solution increases due to the dropping of the hydrogen peroxide solution, the liquid temperature is controlled within a range of 60° C. to 70° C. and preferably 62° C. to 68° C. The amount of dropping the hydrogen peroxide solution may be such that the ratio of the number of moles of the dropped hydrogen peroxide to the number of moles of MBA-HCl contained in the MBA-HCl-containing solution (hydrogen peroxide/MBA-HCl) is preferably about 0.8 or more and about 2.5 or less and more preferably 1 or more and 2 or less. The relationship between the amount of dropping the hydrochloric acid solution and the amount of dropping the hydrogen peroxide solution may be such that the ratio of the number of moles of the dropped hydrogen peroxide to the number of moles of the dropped hydrochloric acid (hydrogen peroxide/hydrochloric acid) is preferably about 0.2 or more and about 1 or less and more preferably 0.35 or more and 0.7 or less. The concentration of hydrogen peroxide in the hydrogen peroxide solution is not particularly limited. If the concentration of hydrogen peroxide is unduly low, the possibility of a prolonged time for the reaction and/or a reduced reactivity will be high because the amount of dropping the hydrogen peroxide solution increases, while if the concentration of hydrogen peroxide is unduly high, the homogeneity of reaction will possibly be low. Therefore, in consideration of such a tendency, the above concentration of hydrogen peroxide may be appropriately set. In general, the concentration of hydrogen peroxide in the hydrogen peroxide solution may preferably be 20 mass % or more and 60 mass % or less and more preferably 25 mass % or more and 50 mass % or less. The dropping time for the hydrogen peroxide solution may appropriately be set with consideration for the concentration of hydrogen peroxide in the hydrogen peroxide solution, etc. An example of the dropping time may be about 1 to 2 hours.

After a predetermined amount of the hydrogen peroxide solution is dropped, the stirring is continued for a predetermined time while maintaining the temperature of the MBA-containing solution within the above temperature range, to complete the reaction. Examples of a target for determining this stirring time include an example in which the stirring time is determined as a time from when the stirring is started to when the ratio of a peak area of MBA-based substances, which peak area is obtained by sampling the MBA-containing solution after the stirring (also referred to as a "reaction liquid" in the present description) and performing HPLC measurement under the condition as stated in the examples to be described later, is 0.5% or less to a peak area of the MBA-based substances obtained by sampling the MBA-containing solution before the dropping of the hydrochloric acid solution. In this case, the stirring time is ordinarily set within a range from several hours to ten and several hours. In the present description, the above ratio of peak areas of the MBA-based substances is also referred to as an "MBA remaining amount."

In view of appropriately performing the chlorination reaction, after the stirring is completed, further dropping of the hydrogen peroxide solution and further stirring may be additionally performed. The amount of hydrogen peroxide in relation to this additional dropping is not particularly limited and one example may be an amount of about 10% or less of the hydrogen peroxide which has been dropped. The stirring time after the hydrogen peroxide is additionally dropped is also not particularly limited and one example may be a comparable time with the stirring time after the first dropping of the hydrogen peroxide solution. The additional dropping of hydrogen peroxide and the subsequent stirring may be performed a plurality of times.

As described above, according to the production method of the present embodiment, the chlorination is carried out only in a liquid phase using a hydrochloric acid solution and a hydrogen peroxide solution. Therefore, the load to facilities required for the reaction is low and the operational safety is excellent compared, for example, with the case of introducing chlorine gas into the MBA-containing solution to carry out the chlorination reaction. Moreover, impurities are less likely to remain in the CMBA-HCl-containing composition because only water remains in the liquid phase even when the hydrogen peroxide used in the production method according to the present embodiment decomposes. That is, the chlorination step in the production method according to the present embodiment is a step of obtaining the CMBA-HCl-containing composition in a simplified manner while reducing the possibility of impurity incorporation, using MBA or substances based thereon, in particular the MBA-HCl, as the reaction substance. In the present description, the MBA and substances based thereon may be collectively referred to as "MBA-based substances" or "4-methoxybenzylamine-based substances." Specifically, in the present description, the "MBA-based substances" refer to substances of which the peaks obtained by HPLC measurement under the condition as stated in the examples to be described later overlap the peak of MBA and which thus cannot be distinguished from MBA.

According to the chlorination step in the production method of the present embodiment, the amount of an unreacted part of MBA contained in the MBA-containing solution can be reduced. In the cases of the method using chlorine gas and the method using sulfuryl chloride as described above, a substantial amount of unreacted MBA may remain in the reaction liquid after completion of the chlorination reaction. Specifically, unreacted MBA remains at about 2% in the case of the method using chlorine gas and at about 1% in the case of the method using sulfuryl chloride. Such unreacted MBA has similar chemical properties to those of CMBA as the objective substance and MBA-HCl is thus likely to remain in the CMBA-HCl-containing composition (in other words, the MBA-HCl is difficult to remove even by means of purification), which may cause poor purity of the CMBA-HCl-containing composition. Therefore, according to the production method of the present embodiment, the CMBA-HCl-containing composition can readily be obtained with a small content of impurities. As is known in the art, the content of MBA-based substances such as MBA-HCl or components based thereon may be severely restricted in some use of the CMBA-HCl-containing composition. In such a case, reducing the concentration of MBA-based substances contained in the CMBA-HCl-containing composition by the production method according to the present embodiment relates directly to enhancing the product's value of the CMBA-HCl-containing composition.

As the above, the chlorination reaction is carried out through the dropping of hydrogen peroxide into the MBA-containing solution, to which the hydrochloric acid solution has been dropped, and the subsequent stirring and if necessary further through repeating these operations (dropping and stirring) performed for the reaction liquid. Thereafter, the reaction liquid is cooled until crystals are precipitated. Cooling temperature is not particularly limited. When the liquid temperature comes to about 50° C. or lower, crystals start to precipitate. The subsequent cooling rate is also not particularly limited. Cooling in the air (1-2° C./min) after stopping the heating may be enough. It is preferred that, when the precipitation starts, the cooling is stopped to suppress impurities from getting mixed in the crystals. Specifically, it is preferred to control the liquid temperature within a range of ±5° C., preferably a range of ±2° C., with respect to the precipitation start temperature. The time for continuing this temperature control is not particularly limited, but several hours or less may be exemplified. Thereafter, the liquid temperature may be further reduced to 10° C. or lower, preferably 5° C. or lower, and this state may be maintained for a certain period of time (e.g. several hours) thereby to precipitate crystals.

After crystals are precipitated in the reaction liquid in this manner, the crystals are filtrated and washed with an appropriate washing solvent (e.g. isopropyl alcohol cooled to about 10° C.) and the CMBA-HCl-containing composition is thereby obtained as a wet cake. In the present description, the CMBA-HCl-containing composition obtained in such a manner is also referred to as a "first CMBA-HCl-containing composition."

(3) Recrystallization Step

Recrystallization may be performed for the first CMBA-HCl-containing composition obtained in the above chlorination step thereby to enhance the purity of the CMBA-HCl contained in the composition. The purity can also be enhanced by increasing the number of recrystallization. However, increasing the number of recrystallization leads to poor productivity due to increase of operations and may further result in a reduced yield and an increased amount of the waste liquid. It is therefore preferred that the purity of the CMBA-HCl can be sufficiently enhanced even by one-time recrystallization of the first CMBA-HCl-containing composition.

A basic aqueous solvent that contains a tertiary amine such as triethylamine and trimethylamine is preferred as the recrystallization solvent which realizes such recrystallization. When such a basic aqueous solvent is used as the recrystallization solvent, the dissociation of hydrochloric acid from 3,5-dichloro-4-methoxybenzylamine hydrochloride contained as an impurity in the first CMBA-HCl-containing composition occurs preferentially to the dissociation of hydrochloric acid from the CMBA-HCl on the basis of the difference in the number of chloro groups bonded to the benzene ring. The 3,5-dichloro-4-methoxybenzylamine (also referred to as "DCMBA" in the present description) generated due to such dissociation of hydrochloric acid has a high solubility to the solvent and is therefore difficult to precipitate as crystals even during the recrystallization, and the purity of the precipitated CMBA-HCl can thus be enhanced.

The type of tertiary amine contained in the above basic aqueous solvent is not particularly limited. Triethylamine is preferred in view of the handling ability. The concentration of the tertiary amine in the solvent is also not particularly limited and may be appropriately set with consideration for the type of the tertiary amine, the amount of CMBA-HCl contained in the first CMBA-HCl-containing composition, the concentration of other components in the solvent, and the like. When the tertiary amine is triethylamine, the use amount of triethylamine as a molar ratio to the amount of CMBA-HCl in the first CMBA-HCl-containing composition is preferably within a range of about 2% or more and 20% or less and more preferably within a range of 5% or more and 15% or less.

Other components than the tertiary amine contained in the above basic aqueous solvent are not particularly limited. Only water may be additionally contained or a polar organic compound such as alcohol may also be contained therein. The content when containing such components is preferably within a range of about 5 vol % to 20 vol % to water.

(4) Other Steps

The method for producing a CMBA-HCl-containing composition according to the present embodiment may include either one of the above chlorination step and recrystallization step or may also include both the steps. Moreover, the method may include other steps than the above chlorination step and recrystallization step. Examples of such steps include a charcoal treatment.

2. CMBA-HCl-Containing Composition

In the CMBA-HCl-containing composition produced by the above production method according to the present embodiment, the purity of CMBA-HCl is high and specifically the content (purity) of CMBA-HCl is 99.9% or more. Moreover, the CMBA-HCl-containing composition produced by the above production method according to the present embodiment has less content of MBA-based substances compared with those in a CMBA-HCl-containing composition produced by the production method as disclosed in Patent Literature 1 and the content of MBA-based substances can be 200 ppm or less as MBA equivalent. Furthermore, the CMBA-HCl-containing composition produced by the above production method according to the present embodiment has less content of substances based on dimerization products of CMBF, which substances would exist to have a substantial amount in a CMBA-HCl-containing composition produced by the production method as disclosed in Non-Patent Literature 1 (in the present description, such substances refer to substances of which the peaks obtained by the HPLC measurement under the condition as stated in the examples to be described later overlap the peaks of the dimerization products of CMBF and which thus cannot be distinguished from the dimerization products of CMBF), and the content of such substances is not larger than the lower detection limit (100 ppm) under the analysis condition as below. Similar to the content (purity) of CMBA-HCl, the content of MBA-based substances and the content of substances based on dimerization products of CMBF refer to values that are calculated on the basis of peak area ratios obtained by HPLC measurement under the condition as stated in the examples below.

EXAMPLES

The present invention will then be described in more detail with reference to examples, but the present invention is not limited only to these specific examples. Analysis was conducted using high-performance liquid chromatography (HPLC) under the condition as below and the surface % was used as the basis to evaluate the purity.
(Column) L-column ODS 4.6 mmφ×150 mm (available from Chemicals Evaluation and Research Institute, Japan)
(Mobile phase)
Mobile phase A: prepared by dropping 0.1 mass % of phosphoric acid for HPLC (available from Wako Pure Chemical Industries, Ltd.) into water for HPLC
Mobile phase B: methanol for HPLC (available from KANTO CHEMICAL CO., INC.)
(Mobile phase composition)
Mobile phase A/Mobile phase B: 10 vol %/90 vol % (for 50 minutes after start of the analysis)
(Mobile phase flow rate) 1.0 mL/min
(Measurement wavelength) 210 nm
(Column temperature) 40° C.
(Injection volume) 10 μL
(Sample preparation method) weighing 30 mg in 50 mL measuring flask and diluting therein with mobile phase A (Example 1) Synthesis of MBA-HCl-Containing Composition To a four-neck 1,000 mL flask provided with a thermometer, Dimroth condenser and stirrer, 110 g of MBA having a purity of 96.0% (mass in terms of pure content: 105.7 g (0.77 mol)) and 440 g of toluene were added and they were stirred and heated to 60° C. Thereafter, 91.9 g of 35% hydrochloric acid (theoretical molar ratio to MBA: 1.1) was dropped into the four-neck flask for 30 minutes while maintaining the temperature. After attaching a Dean-Stark head, the reaction liquid was heated to carry out azeotropic dehydration. Reflux started at about 90° C. and the azeotropic dehydration was continued until the inner temperature came to 110° C. while returning the toluene to the reactor. The reactor was cooled to 20° C. and held for 1 hour. The reaction liquid was filtrated to obtain a wet cake, which was washed with 165 g of toluene, and 139.6 g of wet crystals were obtained. The obtained wet crystals were returned to the four-neck flask, to which 275 g of toluene was added to carry out suspension washing. The reaction liquid after the washing was filtrated to obtain a wet cake, which was washed with 165 g of toluene, and 131.8 g of wet crystals were obtained. The obtained wet crystals were dried using a vacuum drier and a dried product of 129.9 g of white crystals was obtained as an MBA-HCl-containing composition. The yield was 97.0 mol % and the HPLC purity was 99.7%.

(Example 2) Synthesis of First CMBA-HCl-Containing Composition

A four-neck 200 mL flask provided with a thermometer, Dimroth condenser and stirrer was charged with 35 g of the wet crystals of the MBA-HCl-containing composition having a purity of 99.7% obtained in Example 1 (mass in terms of dried product: 30.8 g (0.177 mol)), 153.3 g of water was added thereto, and they were stirred. Then, 46.1 g of 33.7% hydrochloric acid (theoretical molar ratio to MBA-HCl: 2.4) was dropped into the four-neck flask under the ordinary temperature for 30 minutes. After the dropping, the inner temperature was increased to 63° C. and 25.6 g of 33.6% hydrogen peroxide water (theoretical molar ratio to MBA-HCl: 1.43) was dropped into the four-neck flask for 30 minutes while maintaining the temperature. The reaction was carried out at 63° C. for 10 hours and the heating was finished when the remaining amount of MBA-based substances was confirmed to be 0.5% or less by the HPLC analysis. The reaction liquid was gradually cooled (about 5-15° C./hour) to carry out crystallization. Precipitation of crystals was confirmed at 48° C. and the state of a liquid temperature of 48° C. was therefore held for 1 hour. The cooling was continued at a cooling rate of 5-15° C./hour to 5° C. and the state of a liquid temperature of 5° C. was held for 1 hour. The reaction liquid after being held was filtrated to obtain a wet cake, which was washed with 48.7 g of isopropyl alcohol cooled to 5° C., and 31.4 g of wet crystals of a first CMBA-HCl-containing composition were obtained. The obtained wet crystals were dried using a vacuum drier and a dried product of 26.5 g of white crystals was obtained as the first CMBA-HCl-containing composition. The yield was 71.1 mol % and the HPLC purity was 99.1%. In the CMBA-HCl-containing composition, 0.08% of MBA-based substances remained and 0.84% of dichloro products were generated as by-products.

(Comparative Example 1) Synthesis of CMBA-HCl-Containing Composition (Change of Starting Material)

A four-neck 200 mL flask provided with a thermometer, Dimroth condenser and stirrer was charged with 11.7 g (0.08 mol) of MBA, 49.0 g of water was added thereto, and they were stirred and heated to 60° C. Thereafter, 28.9 g of 35% hydrochloric acid (theoretical molar ratio to MBA: 3.4) was dropped into the four-neck flask for 30 minutes while maintaining the temperature. After the dropping, the inner temperature was maintained at 63° C. and in this state 10.9 g of 35% hydrogen peroxide water (theoretical molar ratio to MBA: 1.39) was dropped into the four-neck flask for 30 minutes. The reaction was carried out at 63° C. for 16 hours and the heating was finished when the remaining amount of MBA-based substances was confirmed to be 0.05% or less by the HPLC analysis. The reaction liquid was gradually cooled (about 10° C./hour) to carry out crystallization. Precipitation of crystals was confirmed at 45° C., the cooling was continued at a rate of 10° C./hour to 5° C., and the state of a liquid temperature of 5° C. was held for 1 hour. The reaction liquid after being held was filtrated to obtain a wet cake, which was washed with 22.4 g of isopropyl alcohol cooled to 5° C., and 17.2 g of wet crystals of a CMBA-HCl-containing composition were obtained. The obtained wet crystals were dried using a vacuum drier and a dried product of 12.5 g of slightly yellow crystals was obtained as the CMBA-HCl-containing composition. The yield was 71.8 mol % and the HPLC purity was 98.2%. In the CMBA-HCl-containing composition, 0.13% of MBA-based substances remained and 1.57% of dichloro products were generated as by-products.

(Comparative Example 2) Synthesis of CMBA-HCl-Containing Composition (Sulfuryl Chloride)

To a four-neck 500 mL flask provided with a thermometer, Dimroth condenser and stirrer, 20 g (0.146 mol) of MBA was added. In a state in which the reaction liquid was cooled to 20° C. or lower, 250 g of acetic acid was added thereto and stirring was started. Then, 29.3 g of sulfuryl chloride (theoretical molar ratio to MBA: 1.5) was dropped into the four-neck flask for 1 hour while maintaining the reaction liquid temperature at 25° C. or lower. After the dropping, the inner temperature was maintained at 20-25° C. and in this state the reaction was carried out for 26 hours and finished when the remaining amount of MBA-based substances was confirmed to be 0.5% or less by the HPLC analysis. Then, 150 g of toluene was added to the reaction liquid, which was cooled to 5° C. and then held for 1 hour. The reaction liquid after being held was filtrated to obtain a wet cake, which was washed with 20 g of toluene cooled to 5° C. The wet crystals thus obtained were dried using a vacuum drier and a dried product of 22.8 g of white crystals was obtained as a CMBA-HCl-containing composition. The yield was 75.5 mol % and the HPLC purity was 98.9%. In the CMBA-HCl-containing composition, 0.50% of MBA-based substances remained and 0.23% of dichloro products were generated as by-products.

(Example 3) Synthesis of CMBA-HCl-Containing Composition (Recrystallization Step)

To a four-neck 200 mL flask provided with a thermometer, Dimroth condenser and stirrer, 25.0 g of wet crystals of the first CMBA-HCl-containing composition (purity: 99.1%, mass in terms of dried product: 21.1 g (0.10 mol)), 92.5 g of isopropyl alcohol, 13.3 g of water and 1.54 g of triethylamine (theoretical molar ratio to CMBA-HCl: 0.15) were added and they were stirred and heated until a reflux state was obtained. In mid-course, the crystals were completely dissolved. After 1 hour of the reflux, the reaction liquid was gradually cooled (5-15° C./hour) to carry out crystallization. Precipitation of crystals was confirmed at 72° C. and the state of a liquid temperature of 72° C. was therefore held for 1 hour. The cooling was continued at a cooling rate of 5-15° C./hour to 5° C. and the state of a liquid temperature of 5° C. was held for 1 hour. The obtained reaction liquid after being held was filtrated to obtain a wet cake, which was washed with 42.2 g of isopropyl alcohol cooled to 5° C., and 21.0 g of wet crystals were obtained. The obtained wet crystals were dried using a vacuum drier and a dried product of 16.9 g of white crystals was obtained as a CMBA-HCl-containing composition. The recovery rate was 80.5% and the HPLC purity was 99.9%. The content of dichloro products contained in the CMBA-HCl-containing composition was 0.01% and the content of MBA-based substances was 0.02%.

(Example 4) Synthesis of CMBA-HCl-Containing Composition (Recrystallization Step)

To a four-neck 100 mL flask provided with a thermometer, Dimroth condenser and stirrer, 5.0 g of a CMBA-HCl-containing composition (purity: 99.1%, mass in terms of dried product: 4.96 g (0.024 mol)) containing 0.08% of MBA-based substances and 1.17% of dichloro products, 23.4 g of isopropyl alcohol, 2.6 g of water and 0.24 g of triethylamine (theoretical molar ratio to CMBA-HCl: 0.1) were added and they were stirred and heated until a reflux state was obtained. After 1 hour of the reflux, the reaction liquid was gradually cooled (5-15° C./hour) to carry out crystallization. Precipitation of crystals was confirmed at 72° C. and the state of a liquid temperature of 72° C. was therefore held for 1 hour. The cooling was continued at a cooling rate of 5-15° C./hour to 5° C. and the state of a liquid temperature of 5° C. was held for 1 hour. The reaction liquid after being held was filtrated to obtain a wet cake, which was washed with 8.5 g of isopropyl alcohol cooled to 5° C. The wet crystals thus obtained were dried using a vacuum drier and a dried product of 3.78 g of white crystals was obtained as a CMBA-HCl-containing composition. The recovery rate was 75.7% and the HPLC purity was 99.9%. The content of dichloro products contained in the CMBA-HCl-containing composition was 0.06% and the content of MBA-based substances was 0.01%.

(Example 5) Synthesis of CMBA-HCl-Containing Composition (Recrystallization Step)

A process was carried out under the same condition as in Example 4 except that the amount of triethylamine was changed to 0.18 (theoretical molar ratio to CMBA-HCl: 0.075). As a result, a dried product of 4.05 g of white crystals was obtained as a CMBA-HCl-containing composition. The recovery rate was 81.0% and the HPLC purity was 99.9%. The content of dichloro products contained in the CMBA-HCl-containing composition was 0.08% and the content of MBA-based substances was 0.01%.

(Example 6) Synthesis of CMBA-HCl-Containing Composition (Recrystallization Step)

A process was carried out under the same condition as in Example 4 except that the amount of triethylamine was changed to 0.12 (theoretical molar ratio to CMBA-HCl: 0.05). As a result, a dried product of 4.28 g of white crystals was obtained as a CMBA-HCl-containing composition. The recovery rate was 85.6% and the HPLC purity was 99.9%. The content of dichloro products contained in the CMBA-HCl-containing composition was 0.09% and the content of MBA-based substances was 0.02%.

(Example 7) Synthesis of CMBA-HCl-Containing Composition (Recrystallization Step)

To a four-neck 100 mL flask provided with a thermometer, Dimroth condenser and stirrer, 5.0 g of a CMBA-HCl-containing composition (purity: 91.5%, mass in terms of dried product: 4.58 g (0.022 mol)) containing 4.24% of MBA-based substances and 2.42% of dichloro products, 22.5 g of isopropyl alcohol, 3.5 g of water and 0.24 g of triethylamine were added and they were stirred and heated until a reflux state was obtained. After 1 hour of the reflux, the reaction liquid was gradually cooled (5-15° C./hour) to carry out crystallization. Precipitation of crystals was confirmed at 75° C. and the state of a liquid temperature of 75° C. was therefore held for 1 hour. The cooling was continued at a cooling rate of 5-15° C./hour to 5° C. and the state of a liquid temperature of 5° C. was held for 1 hour. The reaction liquid after being held was filtrated to obtain a wet cake, which was washed with 8.5 g of isopropyl alcohol cooled to 5° C. The wet crystals thus obtained were dried using a vacuum drier and a dried product of 3.68 g of white crystals was obtained as a CMBA-HCl-containing composition. The recovery rate was 78.2% and the HPLC purity was 97.4%. The content of dichloro products contained in the CMBA-HCl-containing composition was 0.25% and the content of MBA-based substances was 2.28%.

(Comparative Example 3) Synthesis of CMBA-HCl-Containing Composition (Recrystallization Step)

A process was carried out under the same condition as in Reference Example 1 except that triethylamine was not added. A dried product of 3.68 g of white crystals was obtained as a CMBA-HCl-containing composition. The recovery rate was 78.2% and the HPLC purity was 96.6%. The content of dichloro products contained in the CMBA-HCl-containing composition was 0.72% and the content of MBA-based substances was 2.44%.

(Comparative Example 4) Synthesis of CMBA-HCl (Recrystallization Step)

To a four-neck 2,000 mL flask provided with a thermometer, Dimroth condenser and stirrer, 75.0 g of wet crystals of a CMBA-HCl-containing composition (purity: 99.2%, mass in terms of dried product: 53.6 g (0.258 mol)) containing 0.03% of MBA-based substances and 0.70% of dichloro products, 193 g of methanol and 579 g of toluene were added and they were stirred and heated to 60° C. The reaction liquid was gradually cooled (5-15° C./hour) finally to 5° C. and the state of a liquid temperature of 5° C. was held for 1 hour. The reaction liquid after being held was filtrated to obtain a wet cake, which was washed with 53 g of a toluene-methanol mixed solution cooled to 5° C. The wet crystals thus obtained were dried using a vacuum drier and a dried product of 41.2 g of white crystals was obtained as a CMBA-HCl-containing composition. The recovery rate was 76.8% and the HPLC purity was 99.88%. The content of dichloro products contained in the CMBA-HCl-containing composition was 0.11% and the content of MBA-based substances was 0.01%.

INDUSTRIAL APPLICABILITY

According to the present invention, a CMBA-HCl-containing composition in which the purity of CMBA-HCl is high can be produced at high productivity.

The invention claimed is:

1. A method for producing a composition containing 3-chloro-4-methoxybenzylamine hydrochloride, the method comprising:
   purifying a composition comprising 3-chloro-4-methoxybenzylamine hydrochloride by recrystallizing the composition with a solvent comprising a tertiary amine,
   wherein a molar ratio of the tertiary amine relative to 3-chloro-4-methoxybenzylamine used in the recrystallizing is in a range from 2% to 20%.

2. The method for producing as recited in claim 1,
   wherein the purifying reduces a content of one or more materials selected from the group consisting of 3,5-dichloro-4-methoxybenzylamine and its derivatives, in the composition comprising 3-chloro-4-methoxybenzylamine hydrochloride.

3. A method for producing a composition containing 3-chloro-4-methoxybenzylamine hydrochloride, the method comprising:
   chlorinating 4-methoxybenzylamine hydrochloride, comprising a chlorination reaction that generates 3-chloro-4-methoxybenzylamine hydrochloride from 4-methoxybenzylamine hydrochloride with materials comprising hydrogen peroxide and hydrochloric acid; and
   purifying 3-chloro-4-methoxybenzylamine hydrochloride resulting from the chlorinating by recrystallizing the resulting 3-chloro-4-methoxybenzylamine hydrochloride, with a solvent comprising a tertiary amine,
   wherein a molar ratio of the tertiary amine relative to 3-chloro-4-methoxybenzylamine used in the recrystallizing is in a range from 2% to 20%.

4. The method for producing as recited in claim 3,
   wherein a starting material for the chlorination reaction is a composition comprising 4-methoxybenzylamine hydrochloride, and
   a content of the 4-methoxybenzylamine hydrochloride is 99.5% or more as a content based on a peak area ratio obtained by HPLC measurement.

5. The method for producing as recited in claim 3,
   wherein the purifying reduces a content of one or more materials selected from the group consisting of 3,5-dichloro-4-methoxybenzylamine and its derivatives, in the composition comprising 3-chloro-4-methoxybenzylamine hydrochloride.

* * * * *